(12) United States Patent
Radha et al.

(10) Patent No.: US 7,091,001 B2
(45) Date of Patent: Aug. 15, 2006

(54) PROCESS FOR THE PREPARATION OF HIGH ARGININE PEPTIDES

(75) Inventors: Cheruppanpullil Radha, Mysore (IN); Karadka Govindaraju, Mysore (IN); Thirumakudalu Chikkaraja Sindhu Kanya, Mysore (IN); Purnima Kaul Tiku, Mysore (IN); Sridevi Annapurna Singh, Mysore (IN); Lalitha Ramakrishna Gowda, Mysore (IN); Bhagya Swamylingappa, Mysore (IN); Appu Rao Gopala Rao Appu Rao, Mysore (IN); Vishveshwariah Prakash, Mysore (IN); Pallavur Rajagopalan Ramasarma, Mysore (IN)

(73) Assignee: Council of Scientific & Industrial Research, New Delhi (IN)

(*) Notice: Subject to any disclaimer, the term of this patent is extended or adjusted under 35 U.S.C. 154(b) by 0 days.

(21) Appl. No.: 10/902,084

(22) Filed: Jul. 30, 2004

(65) Prior Publication Data
US 2006/0024777 A1    Feb. 2, 2006

(51) Int. Cl.
*C12P 21/06* (2006.01)
(52) U.S. Cl. .................. 435/68.1; 426/656; 426/44; 426/52
(58) Field of Classification Search ........... 435/68.1; 426/656, 44, 52
See application file for complete search history.

(56) References Cited

U.S. PATENT DOCUMENTS

| | | | |
|---|---|---|---|
| 3,852,480 A * | 12/1974 | Williams | .............. 426/46 |
| 4,324,805 A | 4/1982 | Olsen | |
| 4,402,874 A * | 9/1983 | Johnson et al. | ........... 530/377 |
| 4,443,540 A * | 4/1984 | Chervan et al. | ......... 435/68.1 |
| 4,577,007 A | 3/1986 | DeBergalis | |
| 5,077,062 A | 12/1991 | Ernster | |
| 5,180,597 A | 1/1993 | Hamm | |
| 5,658,714 A | 8/1997 | Westfall et al. | |
| 5,777,080 A * | 7/1998 | Boatright | ............... 530/378 |
| 5,952,193 A | 9/1999 | Shimamura et al. | |
| 6,022,702 A | 2/2000 | Tsumura et al. | |
| 6,054,151 A * | 4/2000 | Kwon et al. | ............... 426/36 |
| 6,420,133 B1 * | 7/2002 | Cheruppanpullil et al. | 435/68.1 |

FOREIGN PATENT DOCUMENTS

| | | |
|---|---|---|
| EP | 0148600 A | 7/1985 |
| EP | 1331273 | 7/2003 |

OTHER PUBLICATIONS

Wattanapat, R et al. Characteristics of acid hydrolysate from defatted peanut flour. Journal of Food Science. 1995. 60(3): 443-445.*
"Production and Characterization of enzymatic hydrolyzate from soy protein isolate," Netto, F. M. And Galeazzi M.A.M., Lebenson. Wiss. U. Technol. 31, 624-631(1998).
"Effect of dietary protein and amino acids on the metabolism of cholesterol carrying lipoproteins in Rats," Park, M.C. AND Liepa, G.V., 1982, J. Nutrition, 112, 1892-1897.
"Lysine: Arginine ratio of a protein influences cholesterol metabolism part I—Studies on sesame protein having low lysine:arginine ration," Rajamohan, T., and Kurup, P.A., 1997, Indian Journal of Experimental Biology, 35, 1218-1223.
"Vegetable protein and Atherosclerosis," Kritchevsky, D., 1979, A.O.C.S., 56, 135-140.
"Lysine: Arginine ratio of protein and its effect on cholesterol metabolism," Rajamohan, T., and Karup, P.A., 1986 Ind. Journal of Biochemistry and Biophysics, 23, 294-296.
Adler-Nissen, J., 1979, J. Agric. Food Chem., 27, 1256-1262.
G. Tomlinson and T. Viswanatha, 1974, Anal Biochem. 60, 15-24.

* cited by examiner

Primary Examiner—Francisco C. Prats
Assistant Examiner—Susan E. Fernandez
(74) Attorney, Agent, or Firm—Greenblum & Bernstein, P.L.C.

(57) ABSTRACT

A process of preparation of non-bitter high arginine peptide from groundnut, which has an arginine to lysine ratio of at least 5 and a yield of 17–20%.

7 Claims, No Drawings

PROCESS FOR THE PREPARATION OF HIGH ARGININE PEPTIDES

FIELD OF THE INVENTION

This present invention relates to a process for the preparation of non-bitter high arginine peptides

BACKGROUND AND PRIOR ART

It is generally believed that animal proteins are hypercholesterolemic while plant proteins are hypocholesterolemic. Studies on number of plant and animal proteins have shown that groundnut protein produces the highest concentration of serum cholesterol in rats fed on cholesterol-free diet. It has been shown that the ratio of lysine to arginine of a protein may affect on serum cholesterol levels and atherogenicity. Numbers of studies have indicated the source of dietary protein and more specifically, the dietary amino acid ratio within these proteins seem to relate to changes in serum cholesterol levels.

Arginine is present in most of the proteins, including meats, nuts, milk, cheese and eggs. In particular, nuts and grains have high arginine to lysine ratio. Arginine is essential to the metabolism of ammonia that is generated from protein breakdown. It is also needed to transport the nitrogen used in muscle metabolism. Arginine is one of the body building amino acids and influences several hormone functions. L-arginine is shown to improve/decrease liver functions, to lower cholesterol levels and to inhibit the growth of certain tumors in animal system. Arginine participates in many other important reactions such as nitric oxide synthesis and augmatine or creatine formation. It's the body's most potent blood vessel expander and main blood pressure regulator. Several studies have shown that lysine:arginine of a protein is a critical factor determining its effect on cholesterol metabolism Feeding excess lysine has been reported to produce hypercholesterolemia in rats. A low lysine: arginine ratio in protein has been shown to reduce serum and aortic cholesterol.

Several protein additives have been developed from plant sources to serve as functional ingredients in formulated food systems. Flours, concentrates and isolates from plant sources such as groundnut, sunflower, cotton seed and rapeseed/mustard possess a broad spectrum of functional properties. The oilseed meals are excellent protein rich raw material for a number of fabricated food products. However, they have limited use due to lack of some of the desirable functional properties. One of the ways of improving the functional attributes of oilseed proteins is the modification of the proteins. Modification of protein can be accomplished by using the chemical or enzymatic methods. Acid and alkali hydrolysis of protein leads to decrease nutritive amino acids, production of toxic constituents like lysino alanine.

Enzymatic methods accomplish protein hydrolysis selectively without causing structural changes in the amino acids that make up the proteins. The peptide profile generated by enzymatic methods is well defined. The protein retains its nutritive value in enzymatic hydrolysis than any traditional acid/alkali hydrolysis.

The most commonly used raw materials in the preparation of protein hydrolysates are oilseed flours, legume flours, casein and animal proteins.

Groundnut is grown primarily as oilseed crop. Major portion of the groundnut is converted to oil. The cake after oil extraction contains 40% protein. The defatted meal contains 45–50% protein. In addition to protein, it is also a good source of vitamins and minerals.

Protein hydrolysates are used in diets of patients suffering from problems of digestion or poor absorption, intestinal diseases due to food allergies. Protein hydrolysates are also used as supplement for people who have special protein needs such as elderly, athletes and people on weight control diets.

The protein hydrolysates can be good additives to improve the functional characteristics and nutritional value of the end products. Some of the drawbacks of the hydrolysates prepared using acid hydrolysis are humin formation, high temperature involvement, color formation, high salt content in the product, destruction of some of the essential amino acids and low yields.

At present, there are no patents available for the production of protein hydrolyzate from groundnut with high degree of hydrolysis (DH) for use in food formulations.

Reference may be made to T. Sumura et. al., (2000) U.S. Pat. No. 6,022,702 wherein, A process for producing a soy protein hydrolyzate with a low content of glycinin is described. Then the process aqueous suspension of soy protein isolate containing glycinin and β-conglycinin hydrolysed with pepsin at a concentration of about 0.001% to 0.5% by weight of the isolate at a pH of 1–2.8 at a temperature of 20–50° C. and neutralized with sodium hydroxide. The hydrolyzate is heated at 140° C. for 15 seconds and spray dried. The drawback of the method is that neutralization of the acid hydrolyzate results in salts formation, which leads to salty taste in the product when added.

Reference may be made to Chervan et. al. (1984) U.S. Pat. No. 4,443,540 wherein, a process for the hydrolysis of protein using a selected protein material by enzymatic method, separation of the hydrolysed protein by ultra filtration to recover the low molecular weight protein. In the process soy protein isolate is hydrolysed at alkaline pH of 7–9 with alkaline protease pronase at a temperature of 25–60° C. The hydrolysed material is separated to a lower molecular level of 10,000 daltons and the high molecular weight fractions are further hydrolysed. The drawback of the method is repeated hydrolysis of the high molecular weight protein. The process is not cost effective and number of steps involved in the preparation is more time consuming.

Reference may be made to Hamm, D. J. (1993) U.S. Pat. No. 5,180,597 wherein, a process for the production of hydrolysed proteins containing no detectable level of monochlorohydroxyproparol has been described. In the process wheat gluten is hydrolysed with prozyme6, a neutral protease at a temperature of 40–50° C. at a pH of 6.5–7.0, enzyme concentration of about 0.5–1% by weight for 4 h. The hydrolysed protein is separated, concentrated, and treated with gaseous hydrochloric add to deamidate free amino acids. The acidified hydrolyzate from the deamidation is then neutralized to pH 5 to 7 with sodium hydroxide. The drawback of the method is that the hydrolysis is not controlled to prevent bitterness.

Reference may be made to Ernster J. H. (1991) U.S. Pat. No. 5,077,062 wherein, a low sodium, low monosodium glutamate soy hydrolyzate is prepared from soy material such as soy flour, soy meal or soy grits by hydrolyzing the soy material with a protease enzyme in water. The hydrolysis carried out at 90° C. for 2 h. The resulting hydrolyzate contains about 45–55 enzymatic hydrolysed soy based protein. The enzymatically hydrolysed soy protein hydrolyzate has an average molecular weight of about 670,000±50,000.

The drawback of the process is that the hydrolysis carried out at high temperature for long time. The process is energy consuming.

Reference may be made to Satoh et. al., (1988) U.S. Pat. No. 4,577,007 wherein, a process for preparing two kinds of hydrolysates is described using protease from soy protein. The soy protein isolate is hyrolysed at pH 7 with papain for 6 h, acidified to pH 3.0 and subjected to centrifugation. The precipitate is neutralised to pH 6.8 and hydrolysed the protein with pepsin for 4 h at 55° C. (pH 6.8). The separation is done by ultra filtration with a molecular weight cut off of 15,000–20,000. The filtrate is freeze dried. The drawback of the process is that it involves acidification to lower the pH to 2.5–5.0 and separation of two kinds of hydrolyzate mixture, which leads to increase the salt content in the product.

Reference may be made to Cheruppanpulil et. al. (2002) U.S. Pat. No. 6,420,133 wherein, a process for preparation of high protein hydrolyzate using mixed flour from different oilseeds such as soybean, sesame and groundnut. Hydrolysis for 2–3 h with fungal enzyme alkaline protease followed hydrolyzing with a plant enzyme papain as second enzyme at temperature of 50–60° C. for 1–2 h. The drawback of the process involves two stage hydrolysis with two different enzymes and also time consuming. The enzyme used in this process is different.

Reference may be made to Yamamoto Ko et. al. (2003) European Patent No. 1331273 A1 wherein, a process for producing a liquid protein hydrolyzate involves dispersing the defatted soybeans in water at pH 3 and 6 and heated to 120–150° C. The denatured proteins are treated with microorganism Koji mould. The drawback of the process is heating the protein at a high temperature in acidic pH may lead destruction of some of the amino acids. The enzyme and the source of protein used are different from the enzyme used in the present study.

Reference may be made to a published paper titled "Production and characterization of enzymatic hydrolyzate from soy protein isolate" Netto, F. M. and Galeazzi M. A. M., Lebenson, Wiss. U. Technol. 31, 624–631 (1998) wherein, the soy protein isolate is enzymatically hydrolysed using pancreatin enzyme to a degree of hydrolysis of 14.5%. The drawback of the protein hydrolyzate preparation is loss of some of the essential amino acids, which have to be supplemented to meet the specific needs.

Reference may be made to Cipollo, K. L. and Wagner, T. J. (1987) European Patent No. 0148600 B1, wherein a process is described to prepare protein hydrolyzate from soy protein isolate after jet cooking or dynamic heating at 104–204° C. The material is cooled and hydrolysed using bromelian and dried. The process involves multi steps during isolation. The enzyme used is different from the present invention.

Reference may be made to Olsen H. S. (1981) U.S. Pat. No. 4,324,805 wherein a method is described to produce soy protein hydrolyzate from fat containing soy material by washing with aqueous medium at an acidic pH; the partially defatted material is treated with enzyme alkalase and deactivating the enzyme by reducing the pH to 4, treated with carbon and concentrated by reverse osmosis and freeze dried. The drawback of the process is that it involves multi steps and the raw material used is partially defatted flour, the left over oil comes into hydrolyzate, which may lead to off flavors. The enzyme inactivation is done by addition of acid, which is likely to lead to increase in salt content of the product.

Reference may be made to published article titled "Effect of dietary protein and amino acids on the metabolism of cholesterol carrying lipoproteins in rats" Park, M. C., and Liepa, G. V., 1982, J. Nutrition, 112, 1892–1897, wherein the effect of various dietary proteins and amino acids on serum lipid metabolism is studied in rat model. Rats fed a diet containing protein from animal sources had greater serum and high density lipoprotein (HDL)—cholesterol concentrations as well as increased lecithin:cholesterol acryltrans ferase (LCAT) activities than those fed a diet containing protein from plant sources. Animal fed arginine—supplemented casein diet showed a decrease in both serum and HDL cholesterol compared casein alone. Addition of lysine to cotton seed protein diet caused an increase in serum and HDL—cholesterol fractions. The drawback is that all the plant proteins are not compatible with lysine and to reduce the cholesterol.

Reference may be made to published article tided "Lysine:Arginine ratio of a protein influences cholesterol metabolism part I—Studies on sesame protein having low lysine:arginine ratio". Rajamohan, T., and Kurup, P. A., 1997, Indian Journal of Experimental Biology, 35, 1218–1223, wherein the effect of globulin fraction with a lysine:arginine ratio 0.67 and the diet containing casein with a ratio of 2.0 were fed to rats to study the effect on cholesterol metabolism. The study indicated that rats fed with sesame globulin showed significantly lower concentrations of cholesterol in the serum and aorta. The study clearly suggests that the lysine:arginine ratios of a protein exert hypocholesterolemic effects.

Reference may be made to published article titled "Vegetable protein and Atheroselerosis". Kritchevsky, D., 1979, A.O.C.S., 56, 136–140, wherein stated that the vegetable proteins appears to be less cholesteremic than animal protein. It is hypothesized that a high ratio of lysine to arginine may be important.

Reference may be made to the published paper titled "Lysine:Arginine ratio of protein and its effect on cholesterol metabolism". Rajamohan, T., and Kurup, P. A., 1986, Ind. Journal of Biochemistry and Biophysics, 23, 294–296, wherein the lysine arginine ratio of the protein had significant effect on the metabolism of cholesterol in rats fed cholesterol diet. The results indicated that lysine:arginine ratio of 1.0 significantly lowered cholesterol in the serum, liver and aorta and increased hepatic cholesterogenesis as well as degradation of cholesterol to bile acid when compared to lysine:arginine ratio of 2.0.

Reference may be made to U.S. Pat. No. 5,952,193, Shimamura et al., 1997, wherein a peptide mixture from whey protein hydrolyzate with specific amount of free amino acid is described. The peptide mixture is low in phenyl alanine content. The present invention relates to the method of producing a peptide mixture with high arginine and low lysine content from groundnut protein hydrolyzate by an enzymatic method.

Reference may be made to U.S. Pat. No. 5,658,714, Westfall et al., 1992, wherein a high quality soy protein isolate with a significant reduction in phytate and aluminium is prepared via ultrafiltration. The present invention is related to production of a peptide mixture and not whole protein and the source of protein is groundnut.

Peptides that have bitter taste often contain high proportions of leucine, valine and aromatic amino acid residues. Very bitter peptides contain proline residues. The specificity of the protease determines the hydrophobicity and amount of such peptides in the protein hydrolysate. Typically bitter peptides have high average hydrophobicity. In the hydrolysed peptides, the ratio of hydrophilic to hydrophobic amino acid was high which makes them non-bitter.

Groundnut protein isolate has been used for the first time to obtain non-bitter high arginine peptide. Fungal protease, which has been used to hydrolyze the raw material, cleaves the groundnut protein in such a way under the specified conditions of temperature, pH and time of hydrolysis to give a non-bitter taste to the hydrolyzate from which an arginine rich peptide fraction is separated based on molecular sieving by ultrafiltration. The selective separation of peptides to enrich the arginine content by ultrafiltration results in a peptide fraction that is non-bitter.

There are no patents available on the preparation of hydrolyzate from groundnut. Many cited literature have used a number of protein sources for preparing the hydrolysates. In the present invention the raw material used to prepare protein hydrolyzate is groundnut.

OBJECT OF THE INVENTION

The main objective of the present invention is to provide a process for the preparation of high arginine peptides.

Another objective of the present invention is to provide a process for the preparation of bitter free protein hydrolyzate with defined degree of hydrolysis of 30–33% from groundnut protein isolate using fungal protease from *Aspergillus* which obviates the drawback as described above.

Yet in another objective of the present invention is to use a plant protein which has higher arginine content as a source of raw material.

Yet another objective of the present invention is to prepare an enriched fraction of peptides with high arginine to lysine ratio of at least 5.5.

DETAILED DESCRIPTION OF THE INVENTION

Accordingly, the present invention relates to a process for the preparation of high arginine containing peptides and the said process comprising the steps:
 a. mixing groundnut flour with water in a ratio in the range of about 1:10 w/v to obtain a slurry with a pH range of 8–9;
 b. centrifuging the slurry of step (a) at a speed in the range of 6000 to 8000 rpm for period in the range of 20 to 30 minutes;
 c. precipitating the supernatant of step (b) at a pH in the range of 4 to 5 to obtain a protein precipitate;
 d. dispersing the precipitate of step (c) in water in a ratio in the range of 1:20 to 1:2 w/v;
 e. neutralizing the dispersed precipitate of step (d) using alkali to a pH range from 6.8 to 7.4;
 f. drying the neutralized precipitate of step (e) to obtain protein isolate powder;
 g. dispersing the protein isolate powder of step (f) in water in a ratio of about 1:10 w/v to obtain an aqueous slurry of protein isolate;
 h. adjusting the pH and temperature of the aqueous slurry of step (h) in the range of 6 to 7 using acid and 40 to 45° C. respectively;
 i. hydrolyzing the slurry of step (h) using protease enzyme at a concentration in the range of 0.8–1.5% for a period in the range of 3 to 6 hours;
 j. inactivating the protease enzyme of the hydrolyzed slurry by heating the slurry of step (i) to a temperature in the ranging from 70 to 75° C.;
 k. cooling the hydrolysed slurry to a temperature in the range of 27 to 32° C.;
 l. centrifuging the cold hydrolysed slurry of step (m) at a rpm in the range of 8000 to 10,000 for a period in the range of 50 to 60 minutes to obtain a clear supernatant;
 m. ultrafiltering the clear supernatant of step (l) through a membrane of 30,000 Daltons molecular weight cut off to obtain a permeate;
 n. further ultrafiltering the permeate of step (m) through a 3,000 Daltons molecular cut off membrane to obtain retentate high in arginine peptides.

In an embodiment of the present invention, yield of the high arginine peptides is 17 to 20%.

In another embodiment of the present invention, wherein the molecular weights of the desired high arginine peptides is in the range of 30,000 Daltons and 3,000 Daltons.

Still in another embodiment of the present invention, wherein the arginine:lysine ratio of the high arginine peptides is in the range of 5.5 to 7.

Yet in another embodiment of the present invention the alkali used in step (e) is selected from a group comprising sodium hydroxide and potassium hydroxide.

In another embodiment of the present invention the drying of step (f) is done by spray drying at an inlet temperature in the range of 180 to 200° C. and outlet temperature of 80 to 90° C., alternatively, drying using freeze drying at 45–55° C. and 35–45 Pa pressure.

Further in another embodiment of the present invention the acid used in step (h) is selected from a group comprising hydrochloric acid and acetic acid.

Yet in another embodiment of the present invention the protease enzyme is used in step (i) is obtained from fungi.

Still in another embodiment of the present invention the fungi is *Aspergilus*.

The present invention also relates to a process for the preparation of peptides containing an arginine:lysine in at ratio of at least 5.5:1, the process comprising:
 a. mixing groundnut flour with water in a ratio in the range of 1:20 to 1:2 w/v to obtain a slurry with a pH range of 8–9;
 b. centrifuging the slurry of (a) at a speed in the range of 6000 to 8000 rpm for period in the range of 20 to 30 minutes to recover the supernatant;
 c. precipitating the supernatant of (b) at a pH in the range of 4 to 5 to obtain a protein precipitate;
 d. dispersing the precipitate of (c) in water in a ratio of about 1:3 w/v;
 e. neutralizing the dispersed precipitate of (d) using alkali to a pH range from 6.8 to 7.4;
 f. drying the neutralized precipitate of (e) to obtain protein isolate powder;
 g. dispersing the protein isolate powder of (f) in water in a ratio of about 1:10 w/v to obtain an aqueous slurry of protein isolate;
 h. adjusting the pH and temperature of the aqueous slurry of (g) in the range of 6 to 7 using acid and 40 to 45° C. respectively;
 i. hydrolyzing the slurry of (h) using protease enzyme at a concentration in the range of 0.8–1.5% for a period in the range of 3 to 6 hours;
 j. inactivating the protease enzyme of the hydrolyzed slurry by heating the slurry of (i) to a temperature in the ranging from 70 to 75° C.;
 k. cooling the hydrolyzed slurry of (j) to a temperature in the range of 27 to 32° C.;

l. centrifuging the hydrolyzed slurry of (k) at a rpm in the range of 8000 to 10,000 for a period in the range of 50 to 60 minutes to obtain a clear supernatant;

m. ultrafiltering the clear supernatant of (I) through a membrane of 30,000 Daltons molecular weight cut off to obtain a permeate;

n. further ultrafiltering the permeate of (m) through a 3,000 Daltons molecular cut off membrane to obtain a retentate peptide mixture having an arginine:lysine ratio of at least 5.5:1.

Novelty of the process:

Novelty and inventive steps of this invention lies in a process for the preparation of high arginine peptides.

The protein hydrolyzate prepared from the groundnut flour provides a preparation of peptides which could be separated into high arginine containing peptides and high arginine:lysine ratio of at least 5.5 for health benefits.

A starting raw material high in arginine content and treating with a specific proteolytic enzyme to yield a non-bitter protein hydrolysate.

Separation of a high arginine and low lysine peptide preparation by physical methods.

EXAMPLES

The process is further illustrated by the examples given below, which should not be however construed to limit the scope of the invention.

Example 1

10 g of spray dried groundnut protein isolate are dispersed in 100 ml of water and the pH is adjusted to 7.5. Enzyme is added at a concentration of 0.8% (having activity of 85,000 U/g) and incubated at 40±5° C. for 4 h. The enzyme is inactivated by raising the temperature to 70±5° C. for 3–5 mins. Cooled and centrifuged. The clear protein dispersion is spray dried. The yield of groundnut protein hydrolyzate is 96.5% with a nitrogen content of 14.5% with a degree of hydrolysis (DH %) of 32% by the TNBS method (Adler—Nissen, J., 1979, J. Agric. Food Chem., 27, 1256–1262). 50 ml of the clear supernatant is subjected to ultrafiltration using 30,000 Da. cut off membrane. The permeate is further passed through a 3,000 Da membrane. The <30,000 Da and >3,000 Da fractions are pooled to get a peptide preparation that is high in arginine and low in lysine with a arg:lys ratio of 5.5 with an yield of 17%. The arginine content of the peptides between <30,000 and >3,000 Da was estimated by the method of Sakaguchi (G. Tomlinson and T. Viswanatha, 1974, Anal. Biochem. 60, 15–24)/amino acid analysis.

Example 2

20 g of spray dried groundnut protein isolate are dispersed in 100 ml of water and the pH is adjusted to 8. Enzyme is added at a concentration of 0.8% (having activity of 85,000 U/g) and incubated at 40±5° C. for 4 h. The enzyme is inactivated by raising the temperature to 70±5° C. for 3–5 mins. Cooled and centrifuged. The clear protein dispersion is spray dried. The yield of groundnut protein hydrolyzate is 96.2% with a nitrogen content of 14.9% with a degree of hydrolysis (DH %) of 31.5% by the TNBS method (Adler—Nissen, J., 1979, J. Agric. Food Chem., 27, 1256–1262). 150 ml of the clear supernatant is subjected to ultrafiltration using 30,000 Da cut off membrane. The permeate is then passed through a 3,000 Da membrane. The <30,000 Da and >3,000 Da fractions are pooled to get a peptide preparation that is high in arginine and low in lysine with a arg:lys ratio of at least 6 and a yield of 19%. The arginine content of the peptides between <30,000 and >3,000 Da was estimated by the method of Sakaguchi (G. Tomlinson and T. Viswanatha, 1974, Anal. Biochem. 60, 15–24)/amino acid analysis.

Example 3

30 g of spray dried groundnut protein isolate are dispersed in 100 ml of water and the pH is adjusted to 8. Enzyme is added at a concentration of 1% (having activity of 85,000 U/g) and incubated at 40±5° C. for 4 h. The enzyme is inactivated by raising the temperature to 70±5° C. for 3–5 mins. Cooled and centrifuged. The clear protein dispersion is spray dried. The yield of groundnut protein hydrolyzate is 96.9% with a nitrogen content of 15.2% with a degree of hydrolysis (DH %) of 33% by the TNBS method (Adler-Nissen, J., 1979, J. Agric. Food Chem., 27, 1256–1262). 200 ml of the clear supernatant is subjected to ultrafiltration using 30,000 Da cut off membrane. The permeate is then passed through a 3,000 Da membrane. The <30,000 Da and >3,000 Da fractions are pooled to get a peptide preparation that is high in arginine and low in lysine with a arg:lys ratio of at least 6.7 with an yield of 20%. The arginine content of the peptides between <30,000 and >3,000 Da was estimated by the method of Sakaguchi (G. Tomlinson and T. Viswanatha, 1974, Anal. Biochem. 60, 15–24)/amino acid analysis.

Example 4

Bitterness of the peptide was assessed by organoleptic assessment by a semi trained and untrained panel of 10 panelists. A 1% solution of the arginine rich peptide was tasted by the above panelists and found to be non-bitter.

The main advantages of this invention are:

1. The hydrolysis is carried out in single step with commercially available fungal enzyme and the resulting hydrolyzate is not bitter with a degree of hydrolysis of 30–35%; the yield is very high 96% with high nitrogen content of 14–15% with low salt content.

2. The process provides a method for the preparation of a peptide preparation with high arginine and low lysine content with a arginine:lysine ratio of at least 5.

3. A high arginine:lysine ratio has health implications and the above preparation can be used as an ingredient for the preparation of health foods for treating cardio-vascular disease.

We claim:

1. A process for the preparation of peptides having an arginine:lysine ratio of at least 5.5:1, the process comprising:

a. mixing groundnut flour with water in a ratio in the range of 1:20 to 1:2 w/v to obtain a slurry with a pH range of 8–9;

b. centrifuging the slurry of (a) at a speed in the range of 6000 to 8000 rpm for period in the range of 20 to 30 minutes to recover the supernatant;

c. precipitating the supernatant of (b) at a pH in the range of 4 to 5 to obtain a protein precipitate;

d. dispersing the precipitate of (c) in water in a ratio of about 1:3 w/v;

e. neutralizing the dispersed precipitate of (d) using alkali to a pH range from 6.8 to 7.4;

f. drying the neutralized precipitate of (e) to obtain protein isolate powder;

g. dispersing the protein isolate powder of (f) in water in a ratio of about 1:10 w/v to obtain an aqueous slurry of protein isolate;
h. adjusting the pH and temperature of the aqueous slurry of (g) in the range of 6 to 7 using acid and 40 to 45° C. respectively;
i. hydrolyzing the slurry of (h) using protease enzyme at a concentration in the range of 0.8–1.5% for a period in the range of 3 to 6 hours;
j. inactivating the protease enzyme of the hydrolyzed slurry by heating the slurry of (i) to a temperature in the range of from 70 to 75° C.;
k. cooling the hydrolyzed slurry of (j) to a temperature in the range of 27 to 32° C.;
l. centrifuging the hydrolyzed slurry of (k) at a rpm in the range of 8000 to 10,000 for a period in the range of 50 to 60 minutes to obtain a clear supernatant;
m. ultrafiltering the clear supernatant of (I) through a membrane of 30,000 Daltons molecular weight cut off to obtain a permeate;
n. further ultrafiltering the permeate of (m) through a 3,000 Daltons molecular weight cut off membrane to obtain a retentate peptide mixture having an arginine:lysine ratio of at least 5.5:1.

2. A process in according to claim 1, wherein the alkali used in (e) is selected from a group comprising sodium hydroxide and potassium hydroxide.

3. A process according to claim 1, wherein the drying of (f) is done by spray drying at an inlet temperature in the range of 180 to 200° C. and outlet temperature of 80 to 90° C., alternatively, drying using freeze drying at 45–55° C. and 35–45 Pa pressure.

4. A process according to claim 1, wherein the acid in (h) is selected from a group comprising hydrochloric acid and acetic acid.

5. A process according to claim 1, wherein the protease enzyme used in (i) is obtained from *Aspergillus Sp*.

6. A process according to claim 1, wherein the yield of said retentate peptide mixture is 17 to 20%.

7. A process according to claim 1, wherein the peptides within the retentate peptide mixture obtained have molecular weights between 30,000 Daltons and 3,000 Daltons and the arginine:lysine in the ratio of 5.5:1.

* * * * *

UNITED STATES PATENT AND TRADEMARK OFFICE
CERTIFICATE OF CORRECTION

PATENT NO. : 7,091,001 B2 Page 1 of 1
APPLICATION NO. : 10/902084
DATED : August 15, 2006
INVENTOR(S) : Radha et al.

It is certified that error appears in the above-identified patent and that said Letters Patent is hereby corrected as shown below:

At column 10, line 1 (claim 2, line 1) of the printed patent, "A process in according" should read --A process according--.

Signed and Sealed this

Sixth Day of November, 2007

JON W. DUDAS
*Director of the United States Patent and Trademark Office*